United States Patent [19]

Fang

[11] Patent Number: 5,045,196

[45] Date of Patent: Sep. 3, 1991

[54] APPARATUS FOR PRE-CONCENTRATION OF A SAMPLE FOR SPECTROSCOPICAL REASONS

[75] Inventor: Zhaolun Fang, Shenyang, China

[73] Assignee: Bodenseewerk Perkin Elmer GmbH, Uberlingen, Fed. Rep. of Germany

[21] Appl. No.: 444,185

[22] Filed: Nov. 30, 1989

[30] Foreign Application Priority Data

Dec. 16, 1988 [DE] Fed. Rep. of Germany ....... 3842315

[51] Int. Cl.$^5$ ............................................. B01D 15/04
[52] U.S. Cl. ..................................... 210/278; 210/287; 422/101; 422/103; 436/178
[58] Field of Search .............. 210/662, 670, 678, 96.1, 210/269, 275, 278, 287; 422/69, 70, 100, 103, 101; 436/173, 178, 180

[56] References Cited

U.S. PATENT DOCUMENTS

| 1,745,421 | 2/1930 | Higgins | 210/287 |
| 3,897,213 | 7/1975 | Stevens et al. | 210/662 |
| 4,242,097 | 12/1980 | Rich et al. | 210/662050454198 |

Primary Examiner—Ivars Cintins
Attorney, Agent, or Firm—Thomas P. Murphy; Edwin T. Grimes

[57] ABSTRACT

An apparatus for the pre-concentration of a sample substance for spectroscopical reasons in the flow injection analysis having an ion-exchanger column of conical shape filled with a granular ion-exchanger. For pre-concentration of the sample, the sample liquid flows through the ion-exchanger column from the smaller first end. Then the pre-concentrated elements are eluted by an eluting liquid from the wider second end. Therewith, a very low dispersion of the eluted sample slug results. Thus, a considerable increase in the degree of sensitivity can be achieved with high analysis frequency.

3 Claims, 2 Drawing Sheets

APPARATUS FOR PRE-CONCENTRATION OF A SAMPLE FOR SPECTROSCOPICAL REASONS

FIELD OF THE INVENTION

The invention relates generally to spectroscopy and more specifically the pre-concentration of a sample substance in the flow injection analysis.

BACKGROUND OF THE INVENTION

An arrangement for the pre-concentration of a sample substance for spectroscopical purposes in the flow injection analysis is known from a paper by Olsen et al in the journal "The Analyst", vol 108, 905–917. Into parallel peristaltic conduits, a peristaltic pump feeds water, a buffer liquid in the form of ammonium acetate and an eluting liquid in the form of nitric acid. An injection valve is arranged in the hose conduit, into which water is fed. The injection valve contains a through-passage and a sample loop, which is adapted to be optionally switched into the flow in the hose conduit. Then the through-passage is switched into the hose conduit, a flow of sample liquid is passed through the sample loop, such that the sample loop is filled with sample liquid. After the injection valve has been changed over, the sample loop filled with sample liquid is connected to the hose conduit carrying the water flow, such that the sample liquid is taken along by the water flow. The water and the sample liquid, respectively, are mixed with the buffer liquid and, in a first valve position of a valve arrangement, flow through an ion-exchanger column from a first end of the ion-exchanger column to a second end. The second end communicates with a waste outlet. In the first valve position of the valve arrangement the eluting fluid flows to a nebulizer and is sprayed into the flame of an atomic absorption spectrometer. Now pre-concentration of the sample takes place in the ion-exchanger column. The valve arrangement is subsequently changed over to a second valve position. In this second valve position, the water and ammonium acetate hose conduits communicate with the waste outlet. The second end of the ion-exchanger column communicates with the hose conduit carrying the eluting liquid. The first end of the ion-exchanger column communicates with the nebulizer of the atomic absorption spectrometer. The eluting liquid flows through the ion-exchanger column in a direction opposite to the previous direction and elutes the pre-concentrated elements to be determined in to the nebulizer and thus into the burner of the atomic absorption spectrometer.

From a paper by Hartenstein et al in "Analytical Chemistry" 57 (1985), 21,25 and a paper by Zhaolun Fang et al in "Analytica Chimica Acta" 200 (1987), 35–49, an arrangement is known wherein a first sample liquid with an associated buffer liquid and a second sample liquid with an associated buffer liquid are fed by a first peristaltic pump. The sample liquids are mixed with the associated buffer liquids in tube coils, which are connected downstream to the peristaltic pump. The thus obtained sample and buffer liquids are passed to a first valve. In a first valve position of the first valve the sample and buffer liquids are passed to a first end of an associated ion-exchanger column. The other second ends of the ion-exchanger columns each communicate with a waste outlet. Then the two ion-exchanger columns are loaded in a parallel with the sample liquid, the sample is pre-concentrated in the columns. A second peristaltic pump feeds an eluting liquid and water. In a first position of the valve the water is passed to the nebulizer of a plasma burner. In this first position of the valve the eluting liquid communicates with a waste outlet. In the second position the valve passes the eluting liquid to the second end of one of the ion-exchanger columns, the first end of which then communicates with the nebulizer. The ion-exchanger column exposed to the eluting liquid is selected by a change-over valve.

By the use of two ion-exchanger columns, which are loaded in parallel, the analysis time can be approximately halved. Instead of the eluting liquid, water is passed to the nebulizer while the ion-exchanger columns are loaded. The water washes the nebulizer and stabilizes the plasma.

In all known arrangements of the present type the ion-exchanger columns have substantially constant cross section over their entire length. The ion-exchanger columns according to the paper by Zhaolun Fang et al in "Analytica Chimica Act" 200 (2987), 35–49 have conically tapered ends. This is to ensure uniform flow. However, the essential portion of the ion-exchanger column, in which the sample is pre-concentrated, is cylindrical.

In order to obtain a high pre-concentration of the sample in the ion-exchanger column, a relatively long pre-concentration time is required with the known arrangements. This results in dead times of the spectrometer and to inadmissibly high consumption of inert gas when a plasma burner is used. Reduction of the analysis frequency results in difficulties with the calibration in routine applications. Increased drifts of the experimental conditions occur namely due to the increase time of the experiment. The drifts have to be taken into account by more frequency calibration actions. This, however, further reduces the efficiency of the method. A further problem therein is the dispersion of the eluted sample slug, which counteracts an increase in the degree of sensitivity and thus makes longer pre-concentration times necessary.

SUMMARY OF THE INVENTION

The present invention is directed to an ion-exchanger column for use in spectroscopy. In accordance with the present invention, the ion-exchanger column is tapered from the second end toward the first end.

The use of such a shape of the ion-exchanger column means that, when the ion-exchanger column is loaded, which is effected from the narrow first end of the ion-exchanger column, the sample is pre-concentrated in the area of this narrow first end, i.e., in the "tip" of the ion-exchanger column in an area of reduced diameter. From this area the sample is then eluted in very short time by the eluting fluid. Therefore, a sample slug of high concentration but short duration emerges from the ion-exchanger column. Correspondingly, the spectrometer supplies a high but very short output impulse. Thereby, a high degree of sensitivity can be achieved, which is determined by the height of the impulse, without the pre-concentrated sample quality, which is an analog to the area of the impulse, having to be large and thus the time of pre-concentration having to be undesirable long. It has been shown that, with an ion-exchanger column according to the invention, at high analysis frequency a sensitivity can be achieved which is high compared to the prior art.

Therefore, it is an object of the invention to increase the degree of sensitivity of the measurement in spectroscopical analysis without the time for a single analysis becoming impermissibly high.

It is a further object of the invention to counteract the dispersion of the eluted sample slug in the pre-concentration of a sample substance for spectroscopical reasons in the flow injection analysis.

These and other objects will become more readily apparent in view of the following more detailed description.

PREFERRED EMBODIMENT OF THE INVENTION

Figure 1:
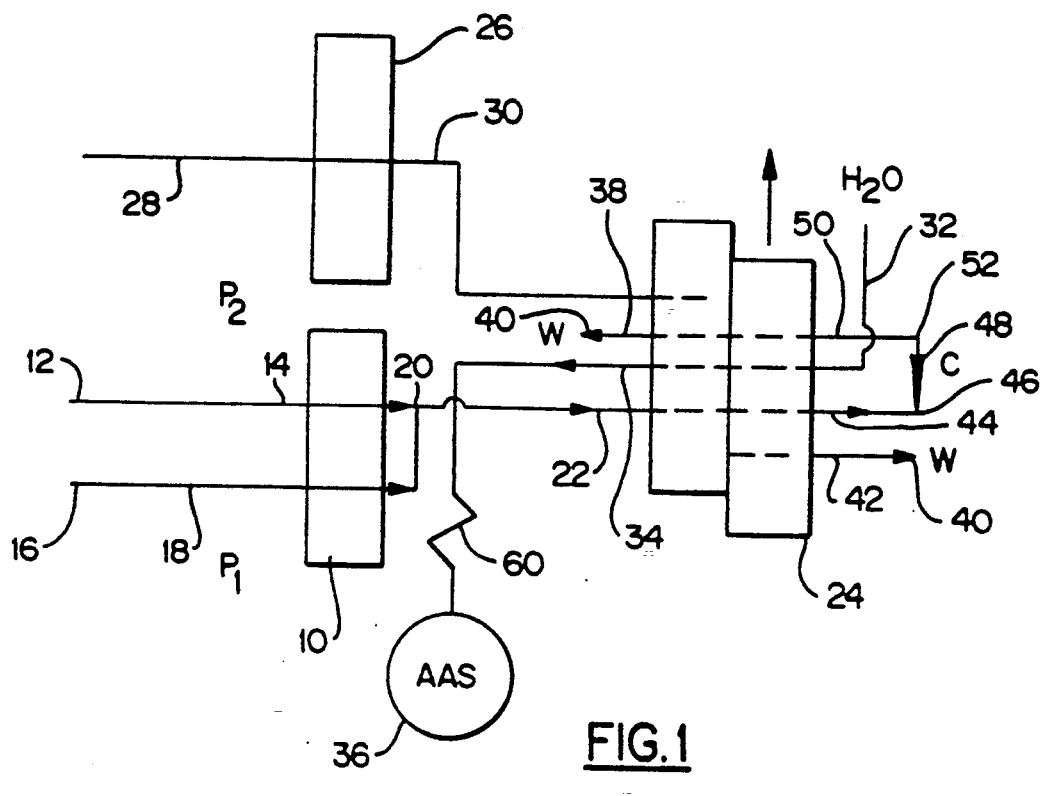
FIG. 1 shows a circuit diagram of an arrangement for the pre-concentration of a sample for spectroscopical purposes by means of an ion-exchanger column in flow injection analysis in the mode of operation "pre-concentration"

In FIG. 1 numeral 10 designates a first peristaltic pump. The peristaltic pump 10 feeds a sample liquid, which is supplied through a port 12 and a hose conduit 14. Furthermore, the peristaltic pump 10 feeds a buffer solution, which is supplied through a port 16 and a hose conduit 18. The two hose conduits 14 and 18 are united in a branching point 20. a common conduit 22 leads from the branching point 20 to a valve 24.

A second peristaltic pump 26 feeds an eluting liquid, e.g., 2-molar hydrochloric acid. The eluting liquid is supplied through a port 28 and a hose conduit 30. the hose conduit 30 likewise communicates with the valve 24.

Furthermore, a conduit 32 communicates with the valve 24, through which conduit 32 de-ionized water is supplied.

A port 34 of the valve 24 communicates with the nebulizer of a burner 36 of an atomic absorption spectrometer, which is only schematically illustrated in FIG. 1. A further port 38 of the valve communicates with a waste outlet 40. A port 42 of the valve 24 likewise communicates with waste outlet 40. A port 44 of the valve 24 communicates with a first end 46 of an ion-exchanger column 48. A port 50 of the valve 24 communicates with a second end 52 of the ion-exchanger column 48. The second end 52 has a larger diameter than the first and 46.

In the first valve position of the valve 24 illustrated in FIG. 1, the common conduit 22 communicates with the first end 46 of the ion-exchanger column 48 through the valve 24 and its port 44. The second end 52 of the ion-exchanger column 48 communicates with the waste outlet 40 through the port 50 of the valve 24, the valve 24 and the port 38. The first pump 10 is switched-on (FIG. 3) and the second pump 26 stands still. Thus, no eluting liquid is fed. De-ionized water is supplied to the nebulizer of the burner 36 through conduit 32, the valve 24 and port 34. In this way the nebulizer is rinsed.

In this first valve position corresponding to the mode of operation "pre-concentration", sample and buffer liquid flow from the first end 46 to the second end 52 through the ion-exchanger column 48. Thereby the elements to be determined are retained and pre-concentrated in the ion-exchanger column.

Figure 2:
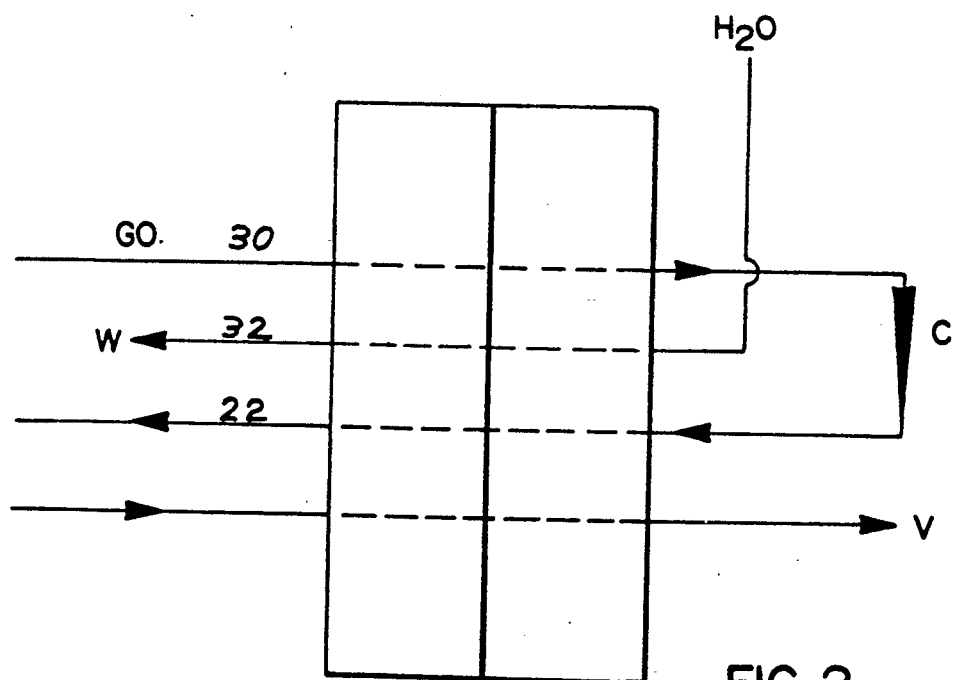
FIG. 2 shows a portion of the arrangement of FIG. 1 in the mode of operation "measurement".

After a period of time of 20 seconds, for example, (FIG. 3) the second pump 26 is switched on. At the same time the valve 24 is changed over into its second valve position. In the second valve position of the valve 24, which is illustrated in FIG. 2, the conduit 22 communicates with the waste outlet 40 through the valve 24 and port 42. Then the peristaltic pump 10 aspirates a new sample and thus displaces the previous one with the elements to be determined and pre-concentrated in the ion-exchanger column from the conduit 22 and the valve 24. The second pump 26 feeds eluting liquid through the peristaltic conduit 30, the valve 24 and port 50 to the first end 52 of the ion-exchanger column 48. The second end of the ion-exchanger column 48 communicates with the nebulizer of the burner 36 through the valve 24 and port 22. Thus, the second pump 26 urges eluting liquid from the second end 52 through the ion-exchanger column 48 to the first end 46. Therewith, the elements to be determined and pre-concentrated in the ion-exchanger column are eluted. The elutant is transported into the nebulizer of the burner 36 by the eluting liquid. Therewith, the ion-exchanger column 48 has the function of the usual sample loop in the flow injection analysis. However, the ion-exchanger column 48 also effects a pre-concentration of the sample.

Figure 4:
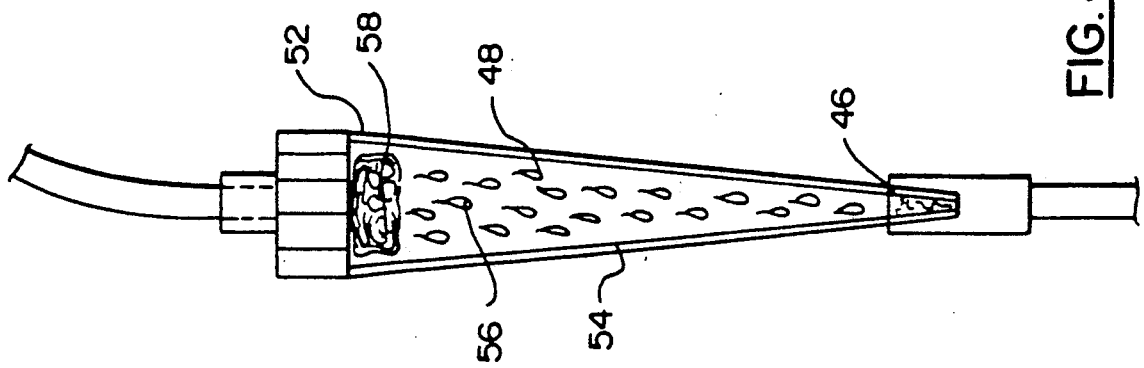
FIG. 4 shows a longitudinal section of an ionexchanger column in the arrangement of FIG. 1.

The ion-exchanger column 48 is tapered from the second end 52 toward the first end 46, which is schematically shown in FIG. 1 and illustrated in detail in FIG. 4. In the illustrated preferred embodiment the ion-exchanger column 48 comprises a conical funnel 54. This funnel 54 is a conventional Eppendorf-pipette tip of plastic, which is cut-off at its pointed first end 46, such that an outlet having an inside diameter of approximately 0.5 mm is obtained. This funnel 54 is densely packed with a granular ion-exchanger 56. The ion-exchanger is 8-quinolinol azoimmobilized on porous glass having a defined pore width with a particle size of 125 –177 $\mu$m and a pore diameter of 500 nm. Such an ionexchanger is delivered by Pierce Chemical Company under the marking CPG/8-Q. The funnel shape of the ion-exchanger column allows the ion-exchanger 56 to be packed very densely. The ion-exchanger 56 is held together by glass wool 58 from the second end 52.

The valve 26 communicates with the nebulizer through the shortest length possible of PTFE-conduit 60. The PTFE-conduit 60 has a length of 5 cm and an internal diameter of 0.5 mm.

Figure 3:
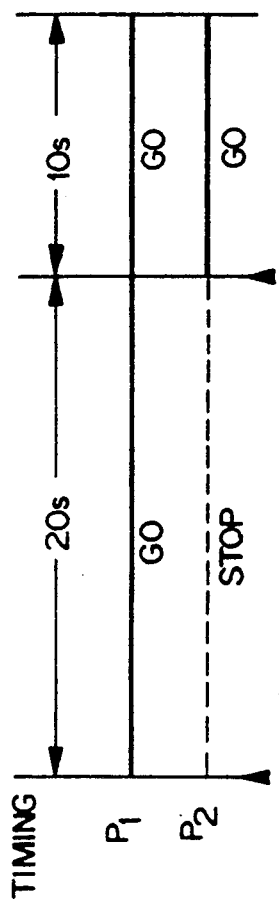
FIG. 3 illustrates the time sequence of a measurement cycle with the arrangement of FIGS. 1 and 2.

As can be seen from FIG. 3, the device is programmed for a pre-concentration time of 20 seconds and an eluting time of 10 seconds. Thus, this results in 120 analyses per hour. The flow rate of the sample liquid for the pre-concentration is 4.8 ml/minute. The buffer liquid is an ammonium acetate solution having a pH-value of 9. The buffer liquid is supplied with a flow rate of 0.2 ml/minute. It is mixed in the branching point 20 with the acid sample liquid having a pH-value of 3. A value of 2.7 ml/minute has turned out to be optimal as the flow rate of the eluting liquid, degassed 2-molar hydrochloric acid. The elutant is supplied to a nebulizer with an aspiration rate of 10 ml/minute.

Figure 5:
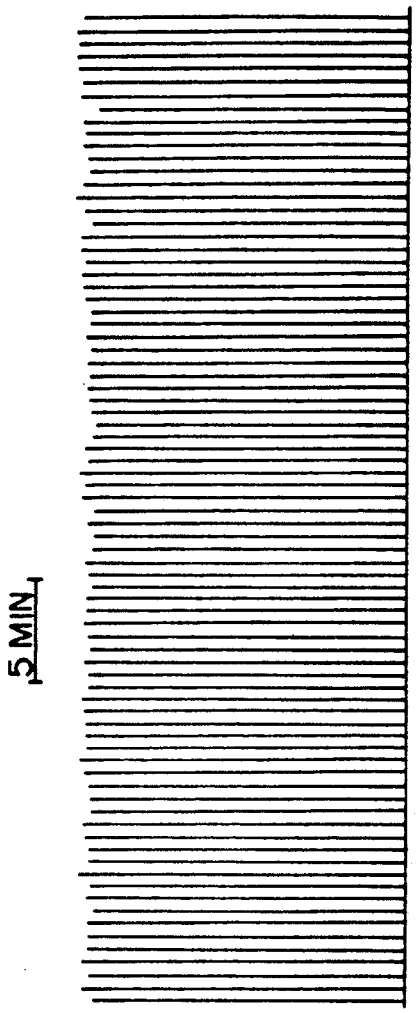
FIG. 5 shows the signals, which were obtained with repeated measurements with an arrangement according to FIG. 1.

FIG. 5 shows signals, which were obtained with repeated measurements of the same sample liquid with an arrangement according to FIGS. 1 to 3. The sample liquid was a copper solution having a concentration of 100 µg/l Cu. A pre-concentration took place with an ion-exchanger column of the type illustrated above having a volume of 65 µl. The sample volume was 1.6 ml. The analysis frequency was 120 measurements per hour. The pre-concentration factor was 25. This resulted in a mean deviation (RSD) of 1.2% of the measurements.

The described arrangement is a system which bridges the large sensitivity gap of 2-3 magnitudes between the flame-ASS and the atomic absorption spectroscopy with a graphite furnace. A 20-30-fold signal increase results relative to the usual flame-AAS with similar analysis frequency and the same sample consumption.

The spectroscopical analytical instrument can be an atomic absorption spectrometer, the eluate being sprayed from the ion-exchanger column into a flame. The flame is arranged in the path of rays of a measuring light beam of the atomic absorption spectrometer. The analytical instrument can also be an atomic absorption spectrometer operating with electrothermal atomization. Finally, the spectroscopical analytical instrument can be an atomic emission spectrometer having a plasma burner. In such an atomic emission spectrometer, a plasma of high temperature is generated in an inert gas flow by a high frequency field. A sample liquid is aspirated into this plasma. The sample liquid is atomized in the plasma. The atoms are stimulated to emission of radiation. Thereby, by means of a polychromator, a plurality of elements can simultaneously be determined in the sample. By pre-concentration of elements to be determined in the ion-exchanger column and subsequently supplying the eluate to the analytical instrument, the sensitivity of the measurement is increased.

Although the preferred embodiment has been illustrated and described, it will be obvious to those skilled in the art that various modifications may be made without departing from the spirit and scope of this invention.

What is claimed is:

1. A device for the pre-concentration of a sample for spectroscopical purposes comprising:
   a conically tapered ion-exchanger column by which elements to be determined are retained and out of which the elements to be determined are elutable by an eluting liquid and having a first and a second end, said second end being larger than said first end, whereby said sample is pre-concentrated;
   first pump means for feeding a sample liquid and a buffer liquid to said ion-exchanger column;
   second pump means for feeding an eluating liquid to said ion-exchanger column;
   a valve having first and second positions, first conduit means associated with the valve for connecting the first end of the ion-exchanger column to the first pump means and the second end of the ion-exchanger column to a waste outlet when said valve is in the first position; and
   second conduit means associated with the valve for connecting the second end of the ion-exchanger column to the second pump means and the first end to a spectroscopical analysis device for eluting the sample from the first end into the spectroscopical analysis device when the valve is in the second position.

2. A device as in claim 1 wherein:
   said valve is adapted to connect a port for a neutral rinsing liquid to a spectroscopical analytical instrument in the first valve positioned and to the waste outlet in the second valve position.

3. A device as in claim 1 wherein:
   said ion-exchanger column contains a densely packed granular material which is held together by glass wool from the second end.

* * * * *